(12) United States Patent
Silverman et al.

(10) Patent No.: US 9,603,820 B2
(45) Date of Patent: Mar. 28, 2017

(54) ORNITHINE AMINOTRANSFERASE INHIBITION WITH GABA ANALOGUES FOR TREATMENT OF HEPATOCELLULAR CARCINOMA

(71) Applicants: Northwestern University, Evanston, IL (US); Hadasit Medical Research Services and Development Ltd., Jerusalem (IL)

(72) Inventors: Richard B. Silverman, Winnetka, IL (US); Yaron Ilan, Kfar Tavor (IL)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 14/936,153

(22) Filed: Nov. 9, 2015

(65) Prior Publication Data

US 2016/0128958 A1 May 12, 2016

Related U.S. Application Data

(60) Provisional application No. 62/076,980, filed on Nov. 7, 2014.

(51) Int. Cl.
 *A61K 31/19* (2006.01)
 *A61K 31/196* (2006.01)

(52) U.S. Cl.
 CPC .................. *A61K 31/196* (2013.01)

(58) Field of Classification Search
 USPC ........................................ 514/573
 See application file for complete search history.

(56) References Cited

U.S. PATENT DOCUMENTS

| 6,794,413 B1 | 9/2004 | Silverman et al. |
| 7,381,748 B1 | 6/2008 | Silverman et al. |
| 7,799,782 B2 * | 9/2010 | Munson .............. C07D 231/56 514/234.5 |
| 8,211,865 B2 | 7/2012 | Ilan et al. |
| 8,686,041 B2 | 4/2014 | Ilan et al. |

FOREIGN PATENT DOCUMENTS

WO 2008023364 A1 2/2008

OTHER PUBLICATIONS

Souba, W., "Glutamine and cancer", Ann. Surgery, 1993, 218, 715-728.
Medina, M., "Glutamine and cancer", J. Nutr., 2001, 131 (9 Suppl), 2539S-2542S.
Lucero et al., "A re-evaluation of the "oncogenic" nature of Wnt/beta-catenin signaling in melanoma and other cancers", Curr Oncol Rep, 2010, 12, 314-318.
Tong, Xuemei et al., "The molecular determinants of de novo nucleotide biosynthesis in cancer cells", Curr. Opin. Genet. Devel., 2009, 19(1), 32-37.
Amadasi A, et al., "Pyridoxal 5' phosphate enzymes as targets for therapeutic agents", Curr Med Chem, 2007, 14, 1291-324.
Dekaney CM, et al. "Regulation of ornithine aminotransferase gene expression and activity by all transretinoic acid in Caco 2 intestinal epithelial cells", J Nutr Biochem, 2008, 19, 674-681.
Liu, Wei et al., "Reprogramming of proline and glutamine metabolism contributes to the proliferative and metabolic responses regulated by oncogenic transcription factor c-MYC" Proc. Natl. Acad. Sci. USA, 2012, 109(23), 8983-8988.
Lu, Hejun et al., "Fluorinated Conformationally Restricted $\gamma$-Aminobutyric Acid Aminotransferase Inhibitors", Journal of Medicinal Chemistry, (2006), 49(25), 7404-7412.
Piettre, S.R. et al., "Reinvestigation of the Wadsworth-Emmons Reaction Involving Lithium Difluoromethylenephosphonate", Tetrahedron Lett., 1996, 37, 5881-5884.
Qiu, J. et al., "A New Class of Conformationally Rigid Analogues of 4-Amino-5-halopentanoic Acids, Potent Inactivators of $\gamma$-Aminobutyric Acid Aminotransferase", J. Med. Chem., 2000, 43, 706-720.
Wang, Zhiyong et al., "Syntheses and Evaluation of Fluorinated Conformationally Restricted Analogues of GABA as Potential Inhibitors of GABA Aminotransferase", Bioorganic & Medicinal Chemistry, (2006), 14(7), 2242-2252.
Yuan, Hai et al., "Structural Modifications of (1S,3S)-3-Amino-4-Difluoromethylenecyclopentanecarboxylic Acid, a Potent Irreversible Inhibitor of GABA Aminotransferase", Bioorganic & Medicinal Chemistry Letters (2007), 17(6), 1651-1654.
Markova, M. et al., "Determinants of Substrate Specificity in $\omega$ Aminotransferases", J. Biol. Chem., 2005, 280 (43), 36409-36416.
Lee, H. et al., "Ornithine Aminotransferase versus GABA Aminotransferase: Implications for the Design of New Anticancer Drugs", Medicinal Research Reviews, Aug. 22, 2014, vol. 35, No. 2, pp. 286-305.
Daune, G. et al., "Interrelationships Between Ornithine, Glutamate, and GABA. II. Consequences of Inhibition of GABA-T and Ornithine Aminotransferase in Brain", Neurochemical Research, 1988, vol. 13, No. 1, pp. 69-75.
International Search Report and Written Opinion for PCT/US2015/059738 dated Jun. 22, 2016, 12 pages.

* cited by examiner

*Primary Examiner* — Rei-Tsang Shiao

(74) *Attorney, Agent, or Firm* — Andrus Intellectual Property Law, LLP

(57) ABSTRACT

Therapeutic methods relating to the use of GABA-AT inhibitor compounds for the treatment of hepatocellular carcinoma.

17 Claims, 3 Drawing Sheets

Figure 1:
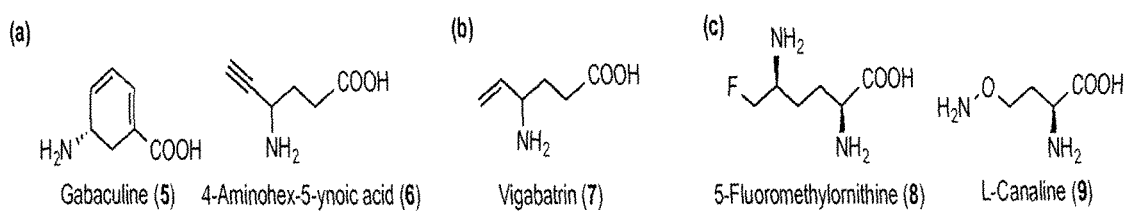

ORNITHINE AMINOTRANSFERASE INHIBITION WITH GABA ANALOGUES FOR TREATMENT OF HEPATOCELLULAR CARCINOMA

This application claims priority to and the benefit of application Ser. No. 62/076,980 filed Nov. 7, 2014—the entirety of which is incorporated herein by reference.

This invention was made with government support under R01 DA030604 awarded by the National Institutes of Health. The government has certain rights in the invention.

BACKGROUND OF THE INVENTION

Hepatocellular carcinoma (HCC) is the most common solid tumor worldwide, the third leading cause of cancer-related deaths worldwide, and the ninth leading cause of cancer deaths in the United States. Moreover, the incidence of HCC in the U.S. is rising because of the spread of hepatitis B and C virus infection. About 90% of primary liver cancers in the U.S. are HCCs. Obese individuals or those with diabetes also are at risk for HCC and a variety of other cancers. HCC is estimated to be responsible for, or involved in, up to approximately 1,250,000 deaths a year, and as such it is numerically one of the world's major malignant diseases.

The prognosis of HCC is poor, with the world-wide frequency rate almost equaling the mortality rate. After diagnosis, the median survival time is less than four months. Long-term survival, defined as survival longer than one year after the diagnosis, is seen only occasionally. Most HCC patients succumb to either the complications of liver failure with or without massive bleeding, or to the general effects of a large tumor burden, with cachexia, malnutrition, infection and sepsis. Though distant metastases occur (up to 90% of patients have metastatic tumors at the time of death), hepatic disease most often limits survival.

Current therapies available to the clinician are on the whole ineffective as a cure for this disease. For patients with advanced HCC who are not candidates for surgical resection, liver transplantation, localized tumor ablation or systemic chemotherapy remains the mainstay of therapy. Unfortunately, HCC is a relatively chemotherapy-resistant proliferative disorder; therefore, outcomes using this mode of treatment are unsatisfactory. Resistance to chemotherapy may be caused by the universal expression of the multidrug resistance gene protein on the surface of the malignant cells, leading to active efflux of chemotherapeutic agents. Chemotherapy is usually not well tolerated and seems to be less efficacious in patients with HCC with underlying hepatic dysfunction. Younger patients with well-compensated cirrhosis due to chronic hepatitis B or C infections have better outcome with chemotherapy than older patients with alcoholic cirrhosis and other comorbid diseases.

The most active single agent drugs tested have been doxorubicin, cisplatin, and fluorouracil. Response rates are about 10%, and treatment shows no clear impact on overall survival. More recently, gemcitabine and capecitabine have been evaluated in clinical trials, but response rates have been low and short term.

Ornithine aminotransferase (OAT) is a mitochondrial matrix enzyme that catalyzes a reversible reaction of interconversion between ornithine and alpha ketoglutarate to delta-1-pyrroline-5-carboxylate and glutamate. The enzyme is expressed in many tissues, including liver, kidney, small intestine, brain and eye. The enzymes from liver and kidney differ significantly in their regulation, and were believed to be two distinct enzymes. However, DNA sequencing proved that the two enzymes are encoded by a single gene.

As indicated above, glutamate is the product of the reaction catalyzed by OAT. This product can be used as a substrate by glutamine synthetase to synthesize glutamine, which is critical for the growth of proliferative cells, supporting protein and nucleotide synthesis and providing a major source of energy. Therefore an increased activity of OAT could make a tumor cell independent of any glutamine supply and confer a growth advantage to the cell. Thus, without being bound by any theory, it may be hypothesized that reducing the level of tissue glutamine concentrations by inactivation of OAT may lead to inhibition in cell proliferation and tumor growth.

SUMMARY OF THE INVENTION

In light of the foregoing, it is an object of the present invention to provide compounds, compositions and related methods of use for the selective inhibition of ornithine aminotransferase, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule, non-peptide compounds exhibiting aminotranferase inhibition.

It can be another object of the present invention to provide one or more such compounds for in vitro use and study under conditions indicative of one or more mammalian disease states.

Alternatively, it can also be an object of the present invention to provide one or more such compounds enabling in vivo treatment of such disease states.

It can also be an object of the present invention, alone or in conjunction with one or more of the foregoing objects, to provide a compound or composition for OAT inhibition or inactivation, inhibition or modulation of cell proliferation and/or treatment of a hepatocellular carcinoma, epilepsy and various other indications.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can be directed to a method for the treatment of a malignant pathologic proliferative disorder in a subject in need thereof. Such a method can comprise administering to such a subject a compound of a formula

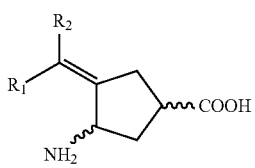

wherein $R_1$ and $R_2$ can be selected from H and F, and at least one of $R_1$ and $R_2$ can be F, or a salt of such a compound. In certain embodiments, $R_1$ and $R_2$ can be F. Without limitation, in certain such embodiments, the amino and carboxy substituents can have a cis stereochemical relationship.

In part, the present invention can be directed to a method for the treatment of a malignant pathologic proliferative disorder in a subject in need thereof. Such a method can comprise administering to such a subject a compound of a formula

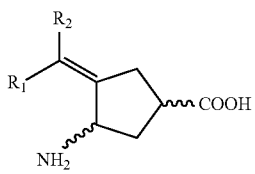

wherein $R_1$ and $R_2$ can be independently selected from H, F, Cl, Br and $(CH_2)_nCF_3$, where n can be an integer selected from 0-2 and where at least one of $R_1$ and $R_2$ is not H, or a salt of such a compound. Without limitation, in certain such embodiments, the amino and carboxy substituents can have a cis stereochemical relationship.

In part, the present invention can also be directed to a method for the treatment of a malignant pathologic proliferative disorder in a subject in need thereof. Such a method can comprise administering to such a subject a compound of a formula

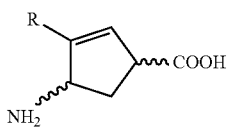

wherein R can be selected from $CF_3$ and $[C(H)_{2-n}(F)_n]_mCF_3$, where n can be an integer selected from 0-2 and m can be an integer selected from 1-2, or a salt of such a compound. Without limitation, in certain such embodiments, the amino and carboxy substituents can have a cis stereochemical relationship.

In part, the present invention can be directed to a method for the treatment of a malignant pathologic proliferative disorder in a subject in need thereof. Such a method can comprise administering to such a subject a compound of a formula

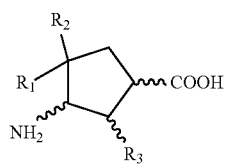

wherein $R_1$ and $R_2$ can be independently selected from H, F, Cl and Br, providing at least one of $R_1$ and $R_2$ is not H, and $R_3$ can be selected from H, F, Cl and Br, or a salt of such a compound. In certain non-limiting embodiments, $R_2$ and $R_3$ can have a cis stereochemical relationship. Regardless, without limitation, in certain such embodiments, the amino and carboxy substituents can have a cis stereochemical relationship.

Regardless, compounds useful in conjunction with this invention are without stereochemical or configurational limitation. As illustrated and discussed below, such compounds and/or their intermediates are available as single enantiomers, racemic mixtures from which isomers can be resolved, or diastereomers from which the corresponding enantiomers can be separated. Accordingly, any stereocenter can be (S) or (R) with respect to any other stereocenter(s). As a separate consideration, regardless of other substitution, e.g., whether monofluoro- or difluorosubstituted, the amino and carboxy substituents can have either a cis or trans stereochemical relationship. Further, with respect to monofluoromethylenyl embodiments, such compounds can have either a Z or E configuration. As another separate consideration, various compounds can be present as an acid salt, either partially or fully protonated. In certain such embodiments, with respect to an ammonio substituent, the counter ion can be a conjugate base of a protic acid. In certain such or other embodiments, with respect to a carboxylate substituent, the counter ion can be an alkaline, alkaline-earth or ammonium cation. Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can also be directed to a method for the treatment of hepatocellular carcinoma in a human subject in need of such a treatment. Such a method can comprise administering (e.g., without limitation, orally) to such a subject a therapeutically effective amount of a compound of the sort discussed above or described elsewhere herein. Without limitation, the dosage of such a compound can be from about 0.001 mg/60 subject kg/day to about 10,000 mg/60 subject kg/day. In certain embodiments, such a compound can be provided as part of a pharmaceutical composition.

In part, the present invention can also be directed to a method of reducing or modulating activity of an ornithine aminotransferase expressed by a human hepatocellular carcinoma. Such a method can comprise providing a compound of the sort discussed above or described elsewhere herein; and contacting such a compound with a cellular medium comprising a hepatocellular carcinoma expressing an ornithine aminotransferase with an amount of such a compound effective to reduce ornithine aminotransferase activity. Such a method can thereby reduce or modulate glutamate production in such a cellular medium. Without limitation, the dosage of such a compound can be from about 0.001 mg/60 subject kg/day to about 10,000 mg/60 subject kg/day. In certain embodiments, such a compound can be provided as part of a pharmaceutical composition. Regardless, such contact can be in vitro or in vivo.

More generally, the present invention can also be directed to a method of reducing or modulating activity of an ornithine aminotransferase expressed by a cancerous tumor. Such a method can comprise providing a compound of the sort discussed above or described elsewhere herein; and contacting such a compound with a cellular medium comprising cancer cells with an amount of such a compound effective to reduce ornithine aminotransferase activity. Such a method can thereby reduce or modulate glutamate production in such a cellular medium. In certain embodiments, such a compound can be provided as part of a pharmaceutical composition. Regardless, such contact can be in vitro or in vivo.

More generally, the present invention can also be directed to a method inhibiting or inactivating an ornithine aminotransferase. Such a method can comprise providing a compound of the sort discussed above or described below, whether or not part of a pharmaceutical composition, and administering an effective amount of such a compound for contact with an ornithine aminotransferase. Such contact can be, as would be understood in the art, for experimental and/or research purposes or as may be designed to simulate one or more in vivo or physiological conditions. Such compounds can include but are not limited to those illustrated by the following examples, referenced figures, incorporated references and/or accompanying synthetic schemes. In certain such embodiments, such a compound and/or combination thereof can be present in an amount at least partially sufficient to inhibit OAT, cell proliferation and/or tumor growth.

Moreover, in yet another departure from the prior art, the present invention can also be directed to a method of using an electron-deficient exocyclic methylene moiety to inhibit ornithine aminotransferase activity. Such a method can comprise providing a compound of a formula

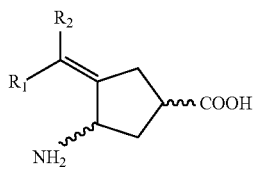

wherein $R_1$ and $R_2$ are selected from H, F and $CF_3$ and at least one of $R_1$ and $R_2$ is F or $CF_3$; such compounds including salts thereof; and contacting such a compound with an ornithine aminotransferase. The exocyclic methylene moiety of such a compound is capable of binding and can, thereby, be bound to an active site residue of the enzyme. Without limitation, such compounds are either monofluoro- or difluoro-, trifluoromethyl- or bis(trifluoromethyl)-substituted, and can vary within the full range of structural, ionic, stereochemical and/or configurational considerations discussed above. Nonetheless, certain cis and trans isomers can be used, as discussed below and provided in the following examples, to demonstrate one or more aspects regarding the utility of this invention.

DETAILED DESCRIPTION OF THE DRAWINGS

FIG. 1. Some known inactivators of (a) both OAT and GABA-AT, (b) only GABA-AT, and (c) only OAT (Prior Art).

Figure 2:
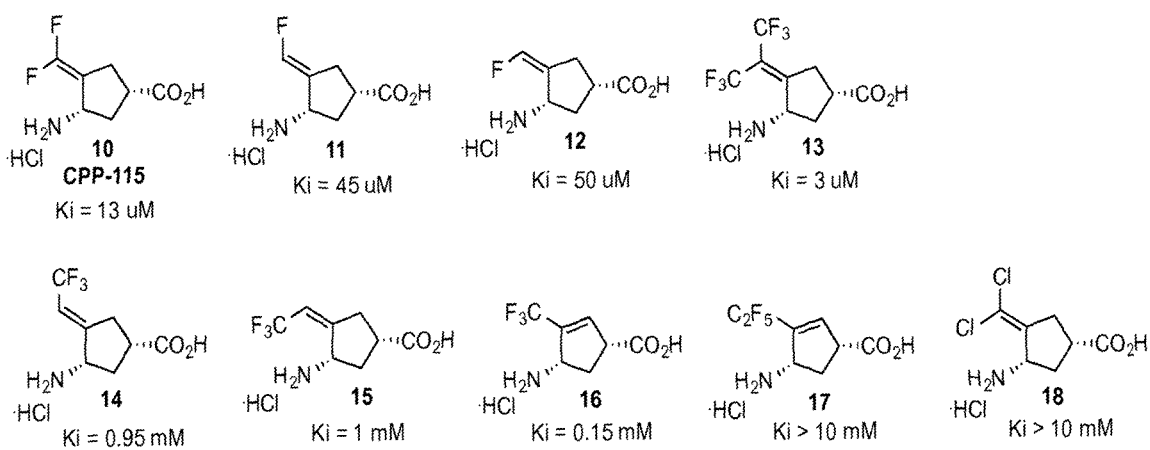

FIG. 2. Inhibition of OAT by various cyclic amino acids, in accordance with certain non-limiting embodiments of this invention (e.g., compounds 10-12).

Figure 3:
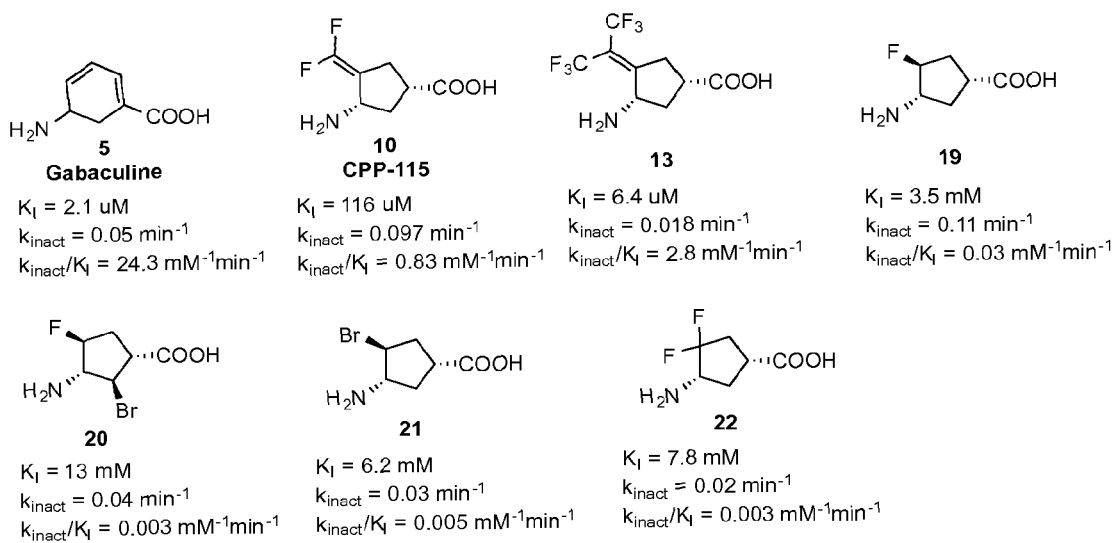

FIG. 3. Time-dependent inactivation of OAT by compound 10, as compared with inactivation by various other cyclic amino acids.

DETAILED DESCRIPTION OF CERTAIN EMBODIMENTS

Various non-limiting embodiments of this invention can be considered with an understanding of the development of HCC and correlation with the activation of the Wnt/β-catenin signaling pathway in liver. The Wnt/β-catenin pathway, an evolutionarily conserved pathway, is essential to normal cellular processes such as growth, development, survival, and regeneration. The key mediator of Wnt signaling, β-catenin, serves several general cellular functions: in a dynamic mode it functions in multiple cellular locations, including the plasma membrane, where β-catenin is important for stabilization of intercellular adhesive complexes; in the cytoplasm, where its levels are regulated; and in the nucleus, where it is involved in transcriptional regulation and chromatin interactions. β-Catenin serves three major roles in liver physiology. In the presence of Wnt, β-catenin translocates to the nucleus, where it functions to activate genes essential for proliferation, growth, and regeneration of the liver. β-Catenin mediates cell-cell adhesion by interacting with E-cadherin on the hepatocyte membrane. In the presence of hepatocyte growth factor (HGF), β-catenin associates with Met (Met is the receptor for HGF) at the surface of hepatocytes, where it is phosphorylated and translocates to the nucleus to upregulate genes for proliferation and morphogenesis. However, in addition to its diverse important physiological functions in liver, β-catenin also is associated with the initiation and progression of cancer, generally as a result of mutations in members of the Wnt/β-catenin pathway. For example, interactions between Met and a mutated active form of β-catenin have been found to facilitate HCC.

Activation of the Wnt/β-catenin signaling pathway, and concomitant development in liver of HCC, correlates with the upregulation of pathway proteins OAT, glutamate transporter GLT-1, and glutamine synthetase. Loss of β-catenin activity blocks glutamine synthesis because of the lack of induction of those three proteins. OAT, which is expressed in many tissues, including liver, kidney, small intestine, brain, and eye, is a pyridoxal 5′-phosphate (PLP)-dependent mitochondrial matrix enzyme that catalyzes the reversible conversion of ornithine (1) and α-ketoglutarate (2) to L-glutamate semialdehyde (which cyclizes to $\Delta^1$-pyrroline-5-carboxylate (3)) and L-glutamate (4) (See, Scheme 1). The L-glutamate formed from OAT is transported away by GLT-1 so that it does not accumulate and become toxic to the cell. The L-glutamate is then converted by glutamine synthetase to L-glutamine.

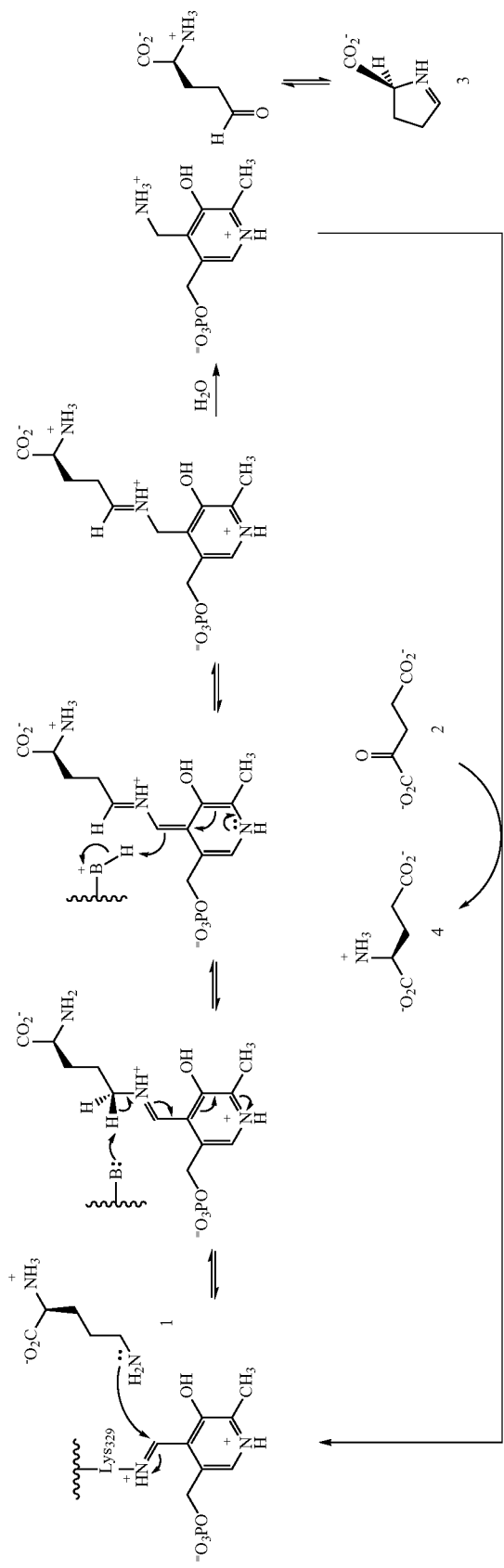
Scheme 1. Ornithine aminotransferase-catalyzed conversion of ornithine (1) to Δ¹-pyrroline-5-carboxylate (3)

Glutamine is the most abundant free amino acid in the body; it is essential for growth of both normal and neoplastic cells. However, tumor cells take up glutamine more efficiently than normal cells, and tumor growth is enhanced by glutamine. (See, e.g., Souba, W. W. Glutamine and cancer. *Ann. Surgery* 1993, 218, 715-728; Medina, M. A. Glutamine and cancer. *J. Nutr.* 2001, 131 (9 Suppl), 2539S-2542S.) With respect to glutamine, cancer cells distinguish themselves from normal cells in that they have an increased requirement for glutamine to support anabolic processes that stimulate proliferation. Glutamine provides a carbon source to maintain pools of tricarboxylic acid (TCA) cycle intermediates and a nitrogen source (for transamination reactions) for nucleotide, nonessential amino acids, and hexosamine biosynthesis. Glutamine also plays a critical role in suppressing oxidative stress because its catabolism can lead to the biosynthesis of glutathione (GSH), a major intracellular antioxidant.

Because glutamine is required for tumor growth, prevention of its enhanced biosynthesis by oncogenes inhibits tumor cell growth. Increased activity of OAT (which makes L-Glu, which is converted to L-Gln) by Wnt/β-catenin activation enhances tumor cell growth independent of glutamine supply, allowing a controlled growth advantage to the tumor cell. Therefore, reducing enhanced glutamine concentrations, which inhibits tumor growth, by OAT inhibition has been suggested. (See, Amadasi A, Bertoldi M, Contestabile R, et al. Pyridoxal 5'-phosphate enzymes as targets for therapeutic agents. *Curr Med Chem* 2007, 14, 1291-324; and Dekaney C M, Wu G, Yin Y L, et al. Regulation of ornithine aminotransferase gene expression and activity by all-transretinoic acid in Caco-2 intestinal epithelial cells. *J Nutr Biochem* 2008, 19, 674-681. See, also, U.S. Pat. Nos. 8,211,865 and 8,686,041, each of which is incorporated herein by reference.)

OAT belongs to the same evolutionary subgroup of PLP-dependent enzymes as γ-aminobutyric acid aminotransferase (GABA-AT), the enzyme found in both glial cells and presynaptic neurons, that catalyzes the conversion of the inhibitory neurotransmitter GABA and α-ketoglutarate to succinic semialdehyde and L-glutamate. These two enzymes share a high structural homology and, like all aminotransferases, also have very similar catalytic mechanisms. Although OAT and GABA-AT have only 17% overall sequence identity, the residues at the active sites of the two enzymes are 57% similar. (Markova, M.; Peneff, C.; Hewlins, M. J. E.; Schirmer, T.; John, R. A., Determinants of Substrate Specificity in ω-Aminotransferases. *J. Biol. Chem.* 2005, 280 (43), 36409-36416.) Structures of ligand-bound OAT and GABA-AT were compared with their unliganded structures, and no large-scale conformational changes were observed. With OAT, the recognition site for the α-carboxylate of ornithine is R180 because R413 binds to E235. This is similar to GABA-AT, where E270 interacts with R445 in a salt bridge; the α-carboxylate of GABA interacts with R192 to correctly position the γ-amino group toward the cofactor for transamination.

Differences between the active site residues of OAT and GABA-AT could determine substrate (inhibitor) selectivity between the enzymes. The major differences are that Tyr55 and Tyr85 of OAT are replaced by Phe351 and Ile72 in GABA-AT. The Phe and Ile residues in the active site of GABA-AT contribute to the narrowing of the active site and its increased hydrophobicity. In OAT the tyrosine residues are the anchor points for the charged amino group at the 2-position of the substrate. With the aid of molecular modeling studies, it has been found that Tyr85 has a significant degree of conformational flexibility, which exposes an accessory binding pocket not present in other aminotransferases that we have investigated.

Because of the structural similarities between OAT and GABA-AT, some inactivators of GABA-AT also inactivate OAT. Consistent with this observation, GABA is a competitive inhibitor of OAT. Gabaculine and 4-aminohex-5-ynoic acid (FIG. 1) are inactivators of GABA-AT, and they also inactivate OAT with equal potency both in vitro and in vivo. Vigabatrin, differing from 4-aminohex-5-ynoic acid with an $sp^2$ vinyl group instead of an sp ethynyl group, does not inactivate OAT. 5-Fluoromethylornithine (5FMOrn) and L-canaline, both analogs of the substrate ornithine, are irreversible inhibitors of OAT but not of GABA-AT. L-Canaline inactivates OAT by forming a stable oxime with the PLP cofactor. On the basis of the crystal structure of OAT inactivated by 5FMOrn, it was suggested that the specificity of 5FMOrn and L-canaline towards OAT might result from interactions with their α-amino groups. With 5FMOrn-inactivated OAT, the α-amino group of 5FMOrn interacts with Tyr55, and the α-carboxyl group is stabilized by Arg180. In GABA-AT, Tyr55 is replaced by Phe321 at this position, so hydrogen bonding with the α-amino group does not occur, presumably the reason inactivation does not take place. Therefore, this one residue difference may be important in the future design of OAT-selective inhibitors, as discussed below.

As noted above, it is well known that oncogene activation of the Wnt/β-catenin signaling pathway corresponds with activation of OAT, leading to a rise in glutamine concentration, which enhances tumor growth. Nonetheless, the prior art has not targeted the Wnt/β-catenin pathway for the treatment of HCC, and has not been directed toward inhibition of OAT as a mechanism for the design of therapeutics for HCC. Because of the lack of effective treatments for liver cancers, there is an important unmet need to identify new pathways for therapeutics. The approach taken through the present invention is the design of mechanism-based inactivators of OAT, leading to irreversible inhibition. Several features distinguish mechanism-based enzyme inhibitors from other compounds as potential therapeutics. First, they are unreactive compounds that are structurally similar to the substrate for the target enzyme and require the catalytic activity of the target enzyme to activate them. Because of this, there is a good probability (once binding selectivity is incorporated) that only the target enzyme will trigger its own catalytic mechanism on these inhibitors, converting them into an activated form that can inactivate the target enzyme, a process known as mechanism-based inhibition. This gives these irreversible inhibitors greater specificity than other inhibitors, since inhibition requires both recognition and catalytic activation for their activity. Second, unlike reversible inhibitors, steady state levels do not need to be maintained to sustain decreased glutamate production, which is driven by de novo synthesis of the enzyme. For example, the half-life for the biosynthesis of rat liver OAT is about 1 day and of rat kidney OAT is about 4 days. If it is similar in HCC, a small amount of inactivator can have lasting effect on decreasing glutamate (and therefore glutamine) concentrations. It is particular desirable to have irreversible inhibition in combating tumor cells. These drugs can have relatively short metabolic half-lives, yet be very effective because of their very long binding half-life. This shuts down glutamine production long enough to have the desired detrimental effect on tumor growth.

Various GABA-AT inhibitor compounds and related compositions are described in U.S. Pat. Nos. 6,794,413 and 7,381,748—each of which is incorporated herein by reference. Without limitation, one such compound is (1S,3S)-3-amino-4-difluoromethylenyl-1-cyclopentanoic acid (10, CPP-115, FIG. 2). This compound does not inhibit alanine aminotransferase, aspartate aminotransferase, or glutamate decarboxylase, even at 6 mM concentration, but it does inhibit/inactivate OAT. It is not active in the Cerep panel of 111 pharmacological targets, does not bind to three human GABA transporters or to $GABA_A$, $GABA_B$, or $GABA_C$, does not bind to the hERG channel, does not inhibit or induce cytochrome P450s, is not metabolized by hepatocytes, has no adverse effect on respiration, and produces no mutations or chromosomal aberrations.

Adopting the reference nos. utilized in the incorporated patents mentioned in the preceding paragraph, compounds useful in conjunction with the present methods can be prepared as shown in Schemes 2 and 3. Illustrating such embodiments, compound 15 was prepared from 12 (Scheme 2). Compound 13 was prepared by a Horner-Wadsworth-Emmons reaction. (Piettre, S. R.; Cabanas, L. Reinvestigation of the Wadsworth-Emmons Reaction Involving Lithium Difluoromethylenephosphonate. *Tetrahedron Lett.* 1996, 37, 5881-5884.) It was then deprotected using ceric ammonium nitrate (CAN) to give 14 and hydrolyzed to give 15. (Qiu, J.; Silverman, R. B. A New Class of Conformationally Rigid Analogues of 4-Amino-5-halopentanoic Acids, Potent Inactivators of γ-Aminobutyric Acid Aminotransferase. *J. Med. Chem.* 2000, 43, 706-720.) (See, more particularly, examples 8-10, below.)

Scheme 2

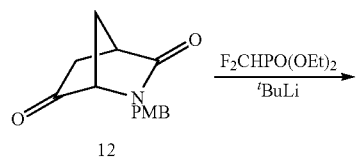

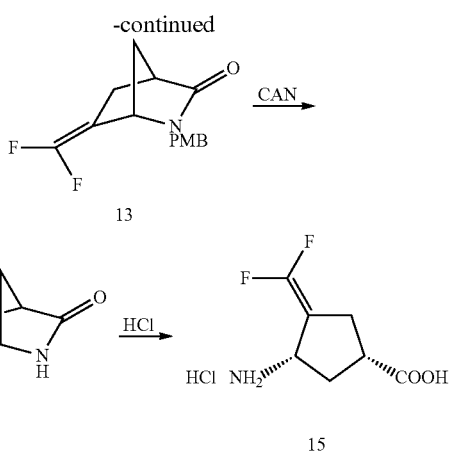

As described in the aforementioned '413 patent, compound 15 was found to be a very potent GABA-AT inactivator even in the presence of 2 mM 2-mercaptoethanol. While the cis isomer is shown in Scheme 2, comparable results can be obtained with the trans isomer, as can be prepared through a straight-forward extension of the synthetic techniques described herein, as would be understood by those skilled in the art.

Likewise, this invention contemplates use of various monofluoro-substituted compounds. The syntheses of compounds 20 and 22 are shown in Scheme 3. The reaction of prior art starting material 12 with fluoromethylphenylsulfone and diethylphosphoryl chloride gave 16 as a mixture of the two isomers, which was then subjected to the reduction with magnesium and mercury chloride, giving 17 and 18 which were separated and isolated. Further deprotection of the lactam then hydrolysis gave 20 and 22. (See examples 15 and 16, below.) Consistent with the foregoing and in accordance with this invention, compounds 20 and 22 also are potent time-dependent inhibitors of GABA-AT. Similar activities can be demonstrated with the corresponding trans isomers.

Scheme 3

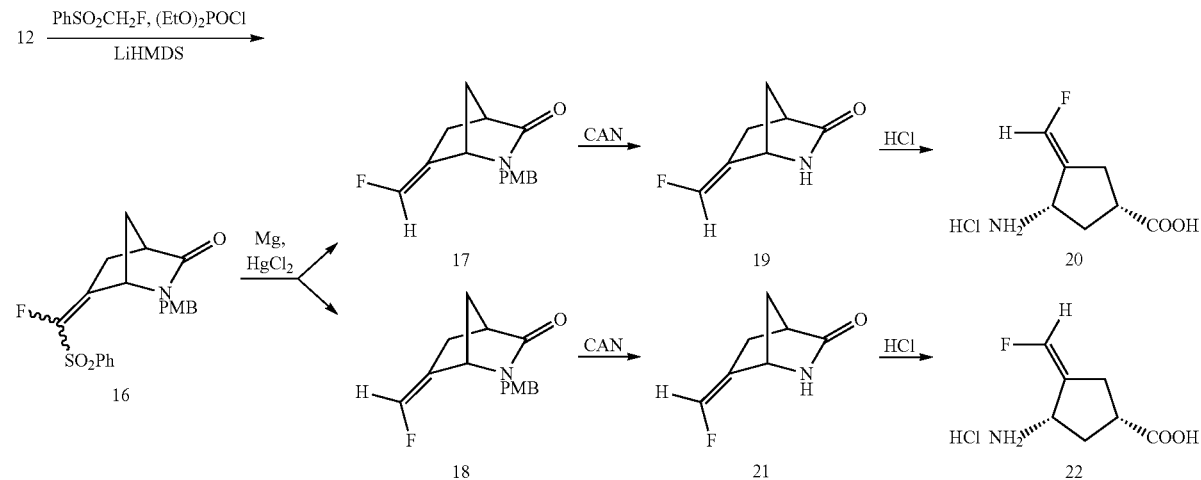

Methods of the present invention can also, as would be understood by those skilled in the art, be extended to or include methods using or in conjunction with a pharmaceutical composition comprising an inhibitor compound of the sort described herein and a physiologically or otherwise suitable formulation. In a some embodiments, the present invention includes one or more OAT inhibitors, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable aqueous or nonaqueous solutions, dispersions, suspensions or emulsions, whether or not sterile. The resulting compositions can be, in conjunction with the various methods described herein, for administration or contact with an ornithine aminotransferase. Whether or not in conjunction with a pharmaceutical composition, "contacting" means that an ornithine aminotransferase and one or more inhibitor compounds are brought together for purpose of binding and/or complexing such an inhibitor compound to the enzyme. Amounts of a compound effective to inhibit an ornithine aminotransferase may be determined empirically, and making such determinations is within the skill in the art Inhibition or otherwise affecting an ornithine aminotransferase activity includes reduction, mitigation and/or modulation, as well as elimination of OAT activity, glutamate production, glutamine synthesis, cell proliferation and/or tumor growth.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more of the present inhibitor compounds for the manufacture of a medicament for therapeutic use in the treatment of hepatocellular carcinoma or the prevention thereof.

Generally, with respect to various embodiments, this invention can be directed to method(s) for the treatment of a pathologic proliferative disorder. As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

According to certain embodiments, a method of the invention can be specifically applicable for the treatment of malignant proliferative disorders. As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. Accordingly, the methods and compositions of the present invention may be used in the treatment of non-solid and solid tumors.

Malignancy, as contemplated in the present invention, may be selected from the group consisting of melanomas, carcinomas, leukemias, lymphomas and sarcomas. Malignancies that can be treated, or as may find utility in the context of the present invention, can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including bladder, rectum, stomach, cervix, ovarian, renal, lung, liver, breast, colon, prostate, GI tract, pancreas and Karposi). More particularly, according to certain embodiments, the compounds used in conjunction with this invention or any composition comprising the same, according to the invention, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma, retinoblastoma, carcinoma of the lacrimal gland, sarcoma of the orbit, brain, spinal cord, vascular system, hemangiosarcoma and Kaposi's sarcoma.

It should be noted that all disorders indicated herein as disorders that may be treated by the methods of the invention, and/or in conjunction with compounds and/or the compositions of the sort described herein. Accordingly, various such compounds and compositions can be administered in conjunction with such a method in any suitable way. For example, administration comprises oral, intravenous, intraarterial, intramuscular, subcutaneous, intraperitoneal, parenteral, transdermal, intravaginal, intranasal, mucosal, sublingual, topical, rectal or subcutaneous administration, or any combination thereof.

According to other embodiments, the treated subject may be a mammalian subject. Although the methods of the invention are particularly intended for the treatment of proliferative disorders in humans, other mammals are included. By way of non-limiting examples, mammalian subjects include monkeys, equines, cattle, canines, felines, mice, rats and pigs.

The terms "treat, treating, treatment" as used herein and in the claims mean ameliorating one or more clinical indicia of disease activity in a subject having a pathologic disorder. "Treatment" refers to therapeutic treatment. Those in need of treatment are mammalian subjects suffering from any pathologic disorder. By "patient" or "subject in need" is meant any mammal for which administration of a compound or any pharmaceutical composition of the sort described herein is desired, in order to prevent, overcome, modulate or slow down such infliction. To provide a "preventive treatment" or "prophylactic treatment" is acting in a protective manner, to defend against or prevent something, especially a condition or disease.

More generally, this invention can be directed to methods to affect, modulate, reduce, inhibit and/or prevent the initiation, progression and/or metastasis (e.g., from the liver elsewhere or to the liver from any other organ or tissue) of a malignant pathologic proliferative disorder associated with activation of the Wnt/β-catenin signaling pathway and increased OAT activity. (See, e.g., Lucero O M, Dawson D W, Moon R T, et al. A re-evaluation of the "oncogenic" nature of Wnt/beta-catenin signaling in melanoma and other cancers. *Curr Oncol Rep* 2010, 12, 314-318; Liu Wei; Le Anne; Hancock Chad; Lane Andrew N; Dang Chi V; Fan Teresa W-M; Phang James M. Reprogramming of proline and glutamine metabolism contributes to the proliferative and metabolic responses regulated by oncogenic transcription factor c-MYC. *Proc. Natl. Acad. Sci. USA* 2012, 109 (23), 8983-8988; and Tong, Xuemei; Zhao, Fangping; Thompson, Craig B. The molecular determinants of de novo nucleotide biosynthesis in cancer cells. *Curr. Opin. Genet. Devel.* 2009, 19(1), 32-37.)

EXAMPLES OF THE INVENTION

The following non-limiting Examples and data illustrate various aspects and features relating to the methods of the present invention, including the treatment of hepatocellular carcinoma and/or reduction of ornithine aminotransferase activity, as can be associated therewith. In comparison with the prior art, the present methods provide results and data which are surprising, unexpected and contrary thereto. While the utility of this invention is illustrated through the use of several compounds and compositions which can be used therewith, it will be understood by those skilled in the art that comparable results are obtainable with various other compound(s), as are commensurate with the scope of this invention.

General Chemical Methods.

All NMR spectra were recorded on either a Varian Mercury 400 MHz or a Varian Inova 500 MHz NMR spectrometer. $^1$H chemical shifts are reported as δ values in ppm downfield from Me$_4$Si as the internal standard in CDCl$_3$. For samples run in D$_2$O, the HOD resonance was set at 4.80 ppm. $^{13}$C chemical shifts are listed in ppm with the CDCl$_3$ carbon peak set to 77.23 ppm. For samples run in D$_2$O, DSS was used as the external standard. $^{19}$F chemical shifts are listed in ppm with CFCl$_3$ as the external standard for samples run in CDCl$_3$ and TFA as the external standard for samples run in D$_2$O. Mass spectra were obtained on a VG70-250SE mass spectrometer. Column chromatography was carried out with Merck silica gel 60 (230-400 mesh ASTM). TLC was run with EM Science silica gel 60 F254 preloaded glass plates. Cation-exchange resin was purchased from Bio-Rad Laboratories. An Orion Research 702 pH meter with a general combination electrode was used for pH measurements. All enzyme assays were recorded on a Perkin-Elmer Lambda 10 UV/Vis spectrometer.

Reagents.

Fluoromethyl phenylsulfone was purchased from TCI America, Inc. All other reagents were purchased from Aldrich Chemical Co. and were used without purification. All solvents were purchased from Fisher Scientific. Anhydrous THF was distilled from sodium metal under nitrogen.

Example 1

*Psammomys obesus*, the sand rat, is a desert gerbil used as a model of proliferative disorder and, because spontaneous hepatic preneoplastic and hepatomas have been described in sand rats, a model for hepatocellular carcinoma. Spontaneous hepatocellular carcinomas (HCCs) were observed in 12-month old sand rats; histologic examination revealed malignant changes include excessive pleomorphism, loss of trabecular pattern, penetration of the tumor across the wall of hepatic veins, and HCC. DNA microarray-based gene expression analysis was performed comparing spontaneous HCC-developing and normal livers. Analysis of the microarray data identified seven genes whose expression levels had increased and 143 genes whose expression levels had decreased in tumor tissues compared to normal livers. OAT was one of the most prominent genes upregulated in all tumors. As discussed above, OAT is a mitochondrial enzyme for transamination of ornithine to glutamine, and was found to be a beta-catenin target gene.

Example 2

Two new continuous assays for OAT were developed for high-throughput readout that are more sensitive than previous methods and measure activity in real time. (Juncosa, J. I.; Lee, H.; Silverman, R. B. Two continuous coupled assays for ornithine-δ-aminotransferase. *Anal. Biochem.* 2013, 440, 145-149.) One assay is based on the reduction of 3 (Scheme 1) by Δ$^1$-pyrroline-5-carboxylate reductase 1 (PYCRI), following the oxidation of NADH spectrophotometrically, and is suitable to study the activity of small molecule inhibitors/inactivators of OAT. (The K$_i$ values for each with OAT is shown in FIG. 2.) The second assay is based on the formation of L-glutamate (4, Scheme 1); this can be used to measure substrate activity of small molecules with OAT. With these two assays in hand, the activity of a variety of compounds made previously as potential inhibitors of GABA-AT were investigated. (Corresponding K$_I$ and k$_{inact}$ values are shown in FIG. 3.)

Time-Dependent Inhibition of OAT by Gabaculine and CPP-115:

OAT activity assays were carried out using as follows. OAT (0.25 μg) is incubated with various concentrations of gabaculine (0.1 μM, 1 μM, 5 μM, 10 μM) or CPP-115 (10 μM, 25 μM, 50 μM, 100 μM, 200 μM) in 100 mM potassium pyrophosphate buffer, pH 8.0, containing 1 mM alpha-ketoglutarate in a total volume of 20 μL at room temperature. At time intervals, 80 μL of assay solution containing PYCR1 (0.5 μg), 12.5 mM alpha-ketoglutarate, 1 mM NADH, 0.03 mM PLP, and 25 mM L-ornithine in 100 mM potassium pyrophosphate buffer, pH 8.0, are added to the incubation mixture and assayed for OAT activity.

With reference to FIG. 2, the most potent inhibitor is 13 (3 μM), which does not inhibit GABA-AT, even at 10 mM concentration. Docking of 13 into the crystal structure of GABA-AT shows that the two trifluoromethyl groups are two large to fit into the long narrow binding pocket. The next best inhibitor of OAT is CPP-115 (10). Docking into the crystal structure of OAT shows lower hydrophobic interactions because of the smaller size of 10 and hydrogen bonding to the fluorine atoms. These seem to be the most important interactions that determine binding efficiency. It is interesting that the corresponding dichloromethylenyl compound (18) is a very weak binder to OAT (and also to GABA-AT). Docking studies comparing 10, 13, and 18 confirmed this conclusion. Compound 10 docks well in the active site, and the fluorine atoms hydrogen bond with Glu235 and Tyr85. The trifluoromethyl groups of 13 are large and do not fit in between Glu235 and Tyr85, but they do fit between Tyr85 and Tyr55, and the fluorine atoms form hydrogen bonds with those residues. The chlorine atoms of 18 are too large to fit in between Glu235 and Tyr85 and chlorine cannot form a hydrogen bond like fluorine; consequently, the dichloromethylene group faces away from this site and has no driving force to fit between Tyr85 and Tyr55.

Example 2b

Inactivation of OAT by CPP-115 and Dialysis of the Inactivated Enzyme

OAT (30 μg) is pre-incubated for 24 h with 2 mM CPP-115 in 100 mM pyrophosphate buffer (pH 8.0) containing 5 mM alpha-ketoglutarate in a total volume of 60 μL at room temperature. OAT incubated without the inactivator serves as a control. After 24 h, the enzyme solutions are transferred to a D-Tube™ Mini dialyzer and exhaustively dialyzed against the buffer (100 mM pyrophosphate buffer containing 0.1 mM alpha-ketoglutarate and 0.1 mM PLP, pH 8.0) at 4° C. protected from light. The dialysis buffer is exchanged three times every 4 h and left overnight. After 48 h of dialysis, the remaining OAT activity in each of the solutions is assayed.

For the determination of $K_I$ and $k_{inact}$ values, the natural logarithm of the percentage of remaining OAT activity is plotted against the pre-incubation time at each inhibitor concentration to obtain the $k_{obs}$ (slope) value for each concentration. The $k_{obs}$ is the rate constant describing the inactivation at each inhibitor concentration. $k_{obs}$ is re-plotted against the inhibitor concentration using nonlinear regression analysis (Graph-Pad Prism 6; GraphPad Software Inc.). $k_{inact}$ and the $K_I$ were estimated from the equation below: kobs=Kinctx[I]/k[I]\+[I], where $k_{inact}$ is the maximal rate of inactivation, $K_I$ is the inhibitor concentration required for half-maximal inactivation, and [I] is the pre-incubation concentration of inhibitor. OAT inactivation by gabaculine and CPP-115 are time- and concentration-dependent. The initial rate constants for the inactivation at various concentrations of the two compounds are determined using non-linear regression analysis.

Some of the cyclic compounds were found to be time-dependent irreversible inhibitors (no activity returned upon dialysis for 48 h in 0.1 M potassium diphosphate buffer pH 8.0 containing 0.1 mM PLP and α-ketoglutarate) of OAT (FIG. 4). Again, 13 is the most efficient, followed by 10. Five compounds (5, 19-22) did not exhibit reversible inhibition at 1 mM concentration, but upon preincubation, enzyme loss occurred; all of these compounds bind poorly to OAT. (The most potent inactivator was gabaculine (5), which is known to inactivate OAT; however, gabaculine is very toxic.)

Example 3

Gabaculine (5) was tested in vitro on eight different HCC cell lines. Forty-eight hours after exposure to 20 mM gabaculine, HCC proliferation was assessed using a $^3$H-thymidine assay. Gabaculine significantly suppressed the proliferation of three HCC cell lines, Hep3B, PLC/PRF/5, and HepA1-6, by 46-51% (FIG. 5A). Alpha-fetoprotein (AFP) secretion was evaluated as a biomarker for HCC. Gabaculine significantly decreased AFP secretion by 20% in Hep3B cells (FIG. 5B). No significant differences in AFP suppression were noted for the other two cell lines. Administration of gabaculine significantly suppressed tumor growth in vivo. Within seven days of a single dose to HCC-harboring mice, AFP serum levels decreased by 92% in comparison with a 9.7 fold increase in controls (FIG. 5C).

Example 4

Assessment of the Effect of Gabaculine on HCC Growth In Vivo

Athymic Balb/C mice were conditioned with sub-lethal radiation (400 cGy). At 24 h after irradiation, animals were injected subcutaneously at the right shoulder with $5 \times 10^6$ human hepatoma Hep3B cells. Blood samples were obtained weekly by retrobulbar puncture, and serum was separated and frozen at −20° C. until assayed. On day 45 the mice were divided into two groups (n=8 per treated and controls) and baseline serum AFP was measured. The experimental group was injected intra-peritoneali once with 500 microgram/kg of gabaculine. Mice in the control group were injected with saline. AFP serum levels, which correlate with tumor growth, were measured on day 52 using a standard Elisa test.

Example 5

Compound 13 was tested in vitro for its effect on suppression of AFP levels in two HCC cell lines, Hep3B and HepG2; a profound suppression of HCC tumor growth was observed (data not shown). Assessment of the safety of 13 was determined by in vivo administration of 0.5-5 mg/kg doses of 13 to C57Bl/6 mice, n=4 per dose group. Each mouse received two doses on days 1 and 4, and mice were tested a week later for liver enzymes, weight, behavior, and fur look. With none of the tested doses were there any notable effects (data not shown). Administration of 13 significantly suppressed tumor growth in vivo. A significant reduction in AFP serum levels and in tumor volume, both normalized to day of starting of therapy, were observed in both treated groups compared to untreated controls. Following 14 days of treatment, serum AFP levels were suppressed, increasing only by 3.4 fold in treated animals compared with a 10.9 fold increase in controls (7224 to 24857 vs. 2671 to 29155 pg/mL, respectively). Tumor size also was suppressed, increasing by only 2.45-fold in treated animals compared with 8.4-fold in controls (0.24 to 0.49 cm$^3$ vs. 0.034 to 0.287 cm$^3$, respectively). Following 21 days of treatment, serum AFP levels increased by 8.15-fold in treated animals vs. 49.8-fold in controls; tumor sizes were suppressed, increasing by 3.05-fold in treated animals vs. 24.2-fold in controls. The antitumor effect was associated with a 20% increase in tumor cell apoptosis. Biopsies were performed from tumors at the end of the experiment for determination of the degree of tumor apoptosis and necrosis using a phosphatidylserine detection kit. The exposure of phosphatidylserine on the outside of the cell was monitored in cell suspensions using fluorochrome labeled Annexin V in flow cytometry.

Example 6

Compound 10 can be tested in vitro and in vivo, as described above, to assess suppression of AFP levels in HCC cell lines and suppression of tumor growth.

Example 7

Statistical Analysis

All analysis can be performed using Excel 2007 (Microsoft, Redmond, Wash., USA). The variables can be expressed as mean±standard deviation (SD). The comparison of two independent groups can be performed using Student's t-test. All tests applied can be two-tailed. P value of 0.05 or less can be considered to be statistically significant.

With reference to Schemes 2 and 3 above, the corresponding discussion and the reference numbers provided in the aforementioned incorporated '413 and '748 patents, Examples 8-16 describe synthesis and characterization of the referenced compounds, in accordance with various embodiments of this invention.

Example 8

(1S,4S)-6-Difluoromethylenyl-2-(4'-methoxybenzyl)-2-azabicyclo[2.2.1]heptan-3-one (13)

At −78° C., $^t$BuLi (1.7 M in pentane, 1.73 mL, 2.94 mmol) was slowly added to a stirred solution of diethyl (difluoromethyl)phosphonate (0.48 mL, 2.94 mmol) in anhydrous THF (15 mL). After being stirred for 0.5 h at −78° C., 12 (0.60 g, 2.45 mmol) in anhydrous THF (20 mL) was slowly added via syringe. Stirring continued for 1 h at −78° C., then the solution was allowed to warm to room temperature and heated to reflux for 24 h. Compound 12 is known and available in the art, and can be prepared as described in Qiu, J.; Silverman, R. B. A New Class of Conformationally Rigid Analogues of 4-Amino-5-halopentanoic Acids, Potent Inactivators of γ-Aminobutyric Acid Aminotransferase. J. Med. Chem. 2000, 43, 706-720. After the reaction had cooled down, THF was evaporated, and saturated NH$_4$Cl solution (20 mL) was added to the residue, which was extracted with EtOAc (3×20 mL). The organic layer was washed with brine (2×20 mL), dried over anhydrous Na$_2$SO$_4$, and concentrated under reduced pressure. The residue was purified by flash column chromatography, eluting with hexanes/ethyl acetate (2:1) to give 13 (0.47 g, 68%) as a colorless oil: $^1$H NMR (400 MHz, CDCl$_3$) δ 7.18 (d, J 8.4 Hz, 2H), 6.07 (d, J 8.4 Hz, 2H), 4.63 (d, J 14.8 Hz, 1H), 4.14 (s, 1H), 3.80 (s, 3H), 3.78 (d, J 14.8 Hz, 1H), 3.00 (s, 1H), 2.50 (dt, J 15.2, 3.6 Hz, 1H), 2.27 (dd, J 15.2, 2.4 Hz, 1H), 2.00 (d, J 9.2 Hz, 1H), 1.53 (d, 9.6 Hz, 1H); $^{13}$C NMR (100 MHz, CDCl$_3$) δ 177.37, 159.13, 152.19 (dd, J 285.7, 281.2 Hz), 129.59, 128.47, 114.13, 88.95 (dd, J 25.6, 22.2 Hz), 58.38 (d, J 5.3 Hz), 55.50, 45.60, 44.59, 40.96, 27.43; $^{19}$F NMR (376 MHz, CDCl$_3$) δ 42.64 and 41.01 (2 dd, J 60.2, 2.3 Hz, 2F). HRMS (EI) C$_{15}$H$_{15}$NO$_2$F$_2$ calcd M 279.1071. found M 279.10701.

Example 9

(1S,4S)-6-Difluoromethylenyl-2-azabicyclo[2.2.1]heptan-3-one (14)

Compound 13 (86.9 mg, 0.31 mmol) was dissolved in CH$_3$CN (1.75 mL). A solution of ceric ammonium nitrate (512 mg, 0.93 mmol) in water (0.87 mL) was slowly added. The resulting solution was stirred at room temperature for 4 h. The reaction mixture was then diluted with ethyl acetate (20 mL), washed with brine (2×10 mL), and dried over anhydrous Na$_2$SO$_4$. After being concentrated under reduced pressure, the residue was purified by flash column chromatography, eluting with hexanes/ethyl acetate (1:1) to give the desired product as a colorless oil (33.6 mg, 68%). $^1$H NMR (400 MHz, CDCl$_3$) δ 5.48 (br s, 1H), 4.40 (s, 1H), 2.93 (s, 1H), 2.54 (dd, J 15.2, 2.8 Hz, 1H), 2.32 (d, J 15.2 Hz, 1H), 2.15 (d, J 9.6 Hz, 1H), 1.64 (d, J 10.0 Hz, 1H); $^{19}$F NMR (376 MHz, CDCl$_3$) δ 42.85 and 40.00 (2d, J 60.2 Hz, 2F); HRMS (EI) C$_7$H$_7$NOF$_2$ calcd M 159.0496. found M 159.04673.

Example 10

(1S,3S)-3-Amino-4-difluoromethylenyl-1-cyclopentanoic acid (15) (i.e., Compound 10, CPP-115, FIG. 2)

To lactam 14 (20.0 mg, 0.13 mmol) was added 4 mL of 4 N HCl. The solution was stirred at 70° C. for 10 h. After being washed with ethyl acetate (3×4 mL), the water layer was evaporated under reduced pressure to give a yellow solid. Recrystallization with ethanol/ether gave a white solid, which was then loaded on a cation-exchange column (AG50W-X8) and eluted with 0.2 N ammonium hydroxide to give the free amino acid 15 as a white solid (16 mg, 72%). $^1$H NMR (400 MHz, D$_2$O) δ 4.44 (s, 1H), 2.92 (m, 1H), 2.74 (m, 1H), 2.57 (dd, J 16.4, 3.6 Hz, 1H), 2.34 (m, 1H), 2.02 (d, J 14.8 Hz, 1H); $^{13}$C NMR (126 MHz, D$_2$O) δ 186.08, 155.30 (t, J 288.7 Hz), 92.19 (m), 53.16 (d, J 3.8 Hz), 48.01, 37.89, 32.45; $^{19}$F NMR (376 MHz, D$_2$O) δ −8.43 and −9.02 (2 d, J 46.3 Hz, 2F); MS (ESI) C$_7$H$_9$NO$_2$F$_2$ calcd M+H 178. found M+H 178.

Example 11

(E/Z)-(1S,4S)-6-(1'-Fluoro-1'-phenylsulfonyl)methylenyl-2-(4'-methoxybenzyl)-2-azabicyclo[2.2.2]heptan-3-one (16)

To anhydrous THF (3 mL) was added fluoromethyl phenylsulfone (130 mg, 0.75 mmol) and diethyl chlorophosphate (0.11 mL, 0.74 mmol). After cooling to −78° C. under nitrogen, lithium bis(trimethylsilyl)amide (1.0 M in THF, 1.65 mL, 1.65 mmol) was slowly added. After stirring for 1 h, a solution of 12 (91.3 mg, 0.37 mmol) in anhydrous THF (3 mL) was slowly added via cannula. The solution was then warmed to room temperature and stirred overnight. After being quenched with saturated NH$_4$Cl solution (10 mL), THF was evaporated and the resulting solution was extracted with ethyl acetate (3×10 mL). The organic layer was combined, washed with brine, and dried over anhydrous Na$_2$SO$_4$. This solution was then concentrated under reduced pressure and purified with flash column chromatography, eluting with hexanes/ethyl acetate (1:0 to 1:2), giving an inseparable cis/trans mixture (16) (4.4:1 as seen from NMR, 119 mg, 80%) as a colorless oil. $^1$H NMR for the major product (400 MHz, CDCl₃) δ 7.94 (d, J 8.0 Hz, 2H), 7.72 (t, J 7.4 Hz, 1H), 7.61 (t, J 7.6 Hz, 2H), 7.33 (d, J 8.4 Hz, 2H), 6.90 (d, J 8.8 Hz, 2H), 5.24 (s, 1H), 4.77 (d, J 14.8 Hz, 1H), 3.82 (s, 3H), 3.79 (d, J 14.8 Hz, 1H), 3.00 (s, 1H), 2.49-2.66 (m, 2H), 2.10 (d, J 9.2 Hz, 1H), 1.63 (d, J 8.8 Hz, 1H).

Example 12

(E)-(1S,4S)-6-Fluoromethylenyl-2-(4'-methoxybenzyl)-2-azabicyclo[2.2.2]heptan-3-one (17) and (Z)-(1S,4S)-6-fluoromethylenyl-2-(4'-methoxybenzyl)-2-azabicyclo[2.2.2]heptan-3-one (18)

Compound 16 (100 mg, 0.25 mmol) was dissolved in anhydrous methanol (10 mL) under nitrogen and put in an ice-salt bath. Magnesium turnings (0.30 g, 12.5 mmol) and mercury (II) chloride (60 mg, 0.22 mmol) were added. The solution was stirred for 2 h, then warmed to room temperature and stirred overnight. The reaction mixture was poured into 1 N HCl (10 mL). Methanol was evaporated under reduced pressure and the resulting water solution was extracted with ethyl acetate (3×10 mL). The organic layer was combined, washed with saturated NaHCO₃ solution (2×10 mL), brine (2×10 mL), and dried over anhydrous Na₂SO₄. After concentration under reduced pressure, the residue was purified by column chromatography with hexanes/ethyl acetate (3:1), giving compound 17 (33.8 mg, 52%) and 18 (12.9 mg, 20%), both as colorless oils.
For 17: ¹H NMR (500 MHz, CDCl₃) δ 7.15 (d, J 8.5 Hz, 2H), 6.87 (d, J 8.5 Hz, 2H), 6.65 (d, J 82.9 Hz, 1H), 4.66 (d, J 15.0 Hz, 1H), 3.83 (s, 1H), 3.81 (s, 3H), 3.72 (d, J 15.0 Hz, 1H), 2.98 (s, 1H), 2.55 (dd, J 16.0, 2.5 Hz, 1H), 2.36 (dd, J 16.0, 1.5 Hz, 1H), 2.02 (d, J 8.0 Hz, 1H), 1.53 (d, J 9.5 Hz, 1H).
For 18: ¹H NMR (500 MHz, CDCl₃) δ 7.21 (d, J 8.5 Hz, 2H), 6.87 (d, J 8.5 Hz, 2H), 6.54 (d, J 84.9 Hz, 1H), 4.67 (d, J 15.0 Hz, 1H), 4.36 (s, 1H), 3.81 (s, 3H), 3.67 (d, J 15.0 Hz, 1H), 2.96 (s, 1H), 2.43 (d, J 14.0 Hz, 1H), 2.21 (d, J 15.0 Hz, 1H), 1.97 (d, J 9.5 Hz, 1H), 1.48 (d, J 9.5 Hz, 1H).

Example 13

(E)-(1S,4S)-6-Fluoromethylenyl-2-azabicyclo[2.2.2]heptan-3-one (19)

In an Eppendorf tube, 17 (10.2 mg, 39 µmol) was dissolved in acetonitrile (0.22 mL). To this solution was added a solution of ceric ammonium nitrate (64 mg, 117 µmol) in water (60 µL). After being stirred at room temperature for 3 h, the reaction mixture was diluted with ethyl acetate (10 mL), washed with brine (2×5 mL), and dried over anhydrous Na₂SO₄. After concentration under reduced pressure, the residue was purified by column chromatography, eluting with hexanes/ethyl acetate (1:1) to give 19 as a colorless oil (2.0 mg, 36%). ¹H NMR (400 MHz, CDCl₃) δ 6.83 (d, J 83.2 Hz, 1H), 5.48 (br s, 1H), 4.15 (s, 1H), 2.90 (s, 1H), 2.60 (d, J 16.8 Hz, 1H), 2.39 (d, J 15.6 Hz, 1H), 2.15 (d, J 9.2 Hz, 1H), 1.61 (d, J 9.2 Hz, 1H); ¹⁹F NMR (376 MHz, CDCl₃) δ −2.75 (d, J 83.6 Hz, 1F).

Example 14

(Z)-(1S,4S)-6-Fluoromethylenyl-2-azabicyclo[2.2.2]heptan-3-one (21)

¹H NMR (400 MHz, CDCl₃) δ 6.47 (d, J 85.6 Hz, 1H), 5.40 (s, 1H), 4.61 (s, 1H), 2.89 (s, 1H), 2.47 (d, J 14.8 Hz, 1H), 2.26 (d, J 16.0 Hz, 1H), 2.13 (d, J 9.2 Hz, 1H); ¹⁹F NMR (376 MHz, CDCl₃) δ −0.27 (d, J 84.0 Hz, 1F).

Example 15

(E)-(1S,3S)-3-Amino-4-fluoromethylenyl-1-cyclopentanoic acid, hydrochloride salt (20) (i.e., Compound 11, FIG. 2)

To compound 19 (2.0 mg, 14 µmol) was added 4 N HCl (4 mL). The solution was heated to 70° C. and stirred for 10 h. Then it was cooled, washed with ethyl acetate (2×4 mL), and evaporated under reduced pressure to give a white solid (2.0 mg, 72%). ¹H NMR (400 MHz, D₂O) δ 6.93 (d, J 81.2 Hz, 1H), 4.33 (m, 1H), 3.06 (t, J 8.0 Hz, 1H), 2.91 (m, 1H), 2.71 (m, 1H), 2.48 (t, J 6.8 Hz, 1H), 2.03 (t, 6.8 Hz, 1H); ¹⁹F NMR (376 MHz, D₂O) δ −48.59 (d, J 78.7 Hz, 1F).

Example 16

(Z)-(1S,3S)-3-Amino-4-fluoromethylenyl-1-cyclopentanoic acid, hydrochloride salt (22) (i.e., Compound 12, FIG. 2)

¹H NMR (400 MHz, D₂O) δ 6.82 (d, J 82.4 Hz, 1H), 4.50 (s, 1H), 3.00 (p, J 8.0 Hz, 1H), 2.70 (m, 1H), 2.48-2.62 (m, 2H), 1.99 (m, 1H); ¹⁹F NMR (376 MHz, D₂O) δ −50.47 (d, J 82.5 Hz, 1F).

Example 17

Compounds 10-22 (FIGS. 2-3) are known and understood by those skilled in the art and made aware of this invention, and are available according to the synthetic procedures and techniques described in the corresponding references, as provided, each of which is incorporated herein, in its entirety.
Compounds 10-12: as described in Examples 8-16 and the aforementioned incorporated '413 and '748 patents.
Compounds 13-17: Lu, Hejun; Silverman, Richard B., Fluorinated Conformationally Restricted γ-Aminobutyric Acid Aminotransferase Inhibitors, Journal of Medicinal Chemistry (2006), 49(25), 7404-7412.
Compound 18: Yuan, Hai; Silverman, Richard B., Structural Modifications of (1S,3S)-3-Amino-4-Difluoromethylenecyclopentanecarboxylic Acid, a Potent Irreversible Inhibitor of GABA Aminotransferase, Bioorganic & Medicinal Chemistry Letters (2007), 17(6), 1651-1654.
Compound 19: Wang, Zhiyong; Silverman, Richard B., Syntheses and Evaluation of Fluorinated Conformationally Restricted Analogues of GABA as Potential Inhibitors of GABA Aminotransferase, Bioorganic & Medicinal Chemistry (2006), 14(7), 2242-2252.
Compounds 20-22: Qiu, Jian; Silverman, Richard B., A New Class of Conformationally Rigid Analogs of 4-Amino-5-Halopentanoic Acids, Potent Inactivators of γ-Aminobutyric Acid Aminotransferase, Journal of Medicinal Chemistry (2000), 43(4), 706-720.

Example 18

Acute Toxicity in Rats

A maximum tolerated dose (Part A) and dose range finding (Part B) study of CPP-115 was conducted in Wistar Albino rats. In Part A of the study, 17 male and 18 female rats, placed in 8 treatment groups, received a single i.p.

injection of CPP-115 at a dose of 0.5, 5, 30, 50, 75, 100, 150, or 300 mg/kg. Clinical findings were observed after a single i.p. administration of CPP-115 at dose levels of 75 mg/kg and above, with all rats treated at the highest dose (300 mg/kg) euthanized in extremis because of low body temperature. Repeat dosing appears to be untenable at these higher levels as the rats exhibited severe apathy from which they did not recover until after 24 hours postdose.

In Part B of the study, 25 male and 25 female Wistar rats, placed in 5 treatment groups, received i.p. injections of CPP-115 once daily for up to 14 days at dose levels of 0, 10, 20, 30, and 50 mg/kg. There appeared to be a cumulative effect with repeated dosing of CPP-115 at doses of 30 mg/kg and above, resulting in weight loss, unkempt appearance, apathy, and unconsciousness. At 20 mg/kg/day, some animals began to lose weight and reduce grooming activities but they did not exhibit apathy or other neurologic symptoms. Rats treated with 20 mg/kg may have developed tolerance to the drug effects because after approximately 5 to 6 days of treatment they began to recover lost body weight and groom themselves adequately. No dose-related clinical findings were observed in the 0 mg/kg or 10 mg/kg groups. No significant weight loss was observed for most rats dosed at 10 mg/kg after 14 days of treatment. A few animals treated with 10 mg/kg, however, displayed sporadic weight loss on isolated study days suggesting the possibility of infrequent sedation at this dose. Clinical chemistry results did not appear to indicate a clear pathophysiologic effect, although the results were consistent with the test article causing sedation and decreased activity, which lead to decreased food consumption. The dose-related decreases in cholesterol, triglycerides, amylase, and alkaline phosphatase could be indicators of malnourishment. Overall, it appears that rats tolerated daily repeat dosing of CPP-115 at levels up to 20 mg/kg for 14 days.

Example 19

Repeated-Dose Toxicity in Rats

A 4-week oral (gavage) toxicology/toxicokinetic study was performed in Crl:CD(SD) rats with CPP-115 at doses of 0 (RO water), 2, 6, and 20 mg/kg/day. Rats received test article once daily for at least 4 weeks at a dose volume of 10 mL/kg followed by a 4-week recovery period. CPP-115 was well tolerated at 2 and 6 mg/kg/day and resulted in no clinical observations or changes in body weight or food consumption. Exposure to CPP-115 increased with the increased dose level. The increases in Cmax and AUC0-t were generally dose proportional. No accumulation of CPP-115 was observed after multiple dosing.

It appears that CPP-115 may not be highly extracted by the liver and may highly distribute to the tissues after oral administration. A test article-related and adverse microscopic finding of retinal dysplasia, characterized primarily by irregular growth patterns in the outer nuclear layer, was noted during the dosing and recovery phases in rats administered 6 or 20 mg/kg/day of CPP-115. Therefore, the no-observed-adverse-effect-level (NOAEL) for CPP-115 was 2 mg/kg/day.

Example 20

Repeated-Dose Toxicity in Dogs

A 4-week oral (gavage) toxicology/toxicokinetic study was performed in beagle dogs with CPP-115 at doses of 0 (RO water), 0.7, 2.3, and 7 mg/kg/day. Dogs received test article once daily for at least 4 weeks at a dose volume of 7 mL/kg followed by a 4-week recovery period. Exposure to CPP-115 increased with the increase in dose level from 0.7 to 7 mg/kg/day. The increase in mean Cmax and AUC0-24 were generally dose proportional. No accumulation of CPP-115 was observed after multiple dosing in dogs.

Assessment of toxicity was based on mortality, clinical observations, body weights, body weight gain, food consumption, physical examinations, vital signs (heart rate, respiration, and body temperature), ophthalmology examinations, electrocardiogram examinations, clinical and anatomic pathology, and left eye evaluation. CPP-115 administered to beagle dogs was well tolerated at all dose levels. No test article-related findings were noted at 0.7 or 2.3 (males only) mg/kg/day. Non-adverse test article-related findings in dogs given 7 mg/kg/day included hypoactivity, minimally or slightly increased vacuoles in the white matter of the cerebellum and brain stem and in the cerebral cortex gray matter, and minimal to slight centrilobular hepatocyte vacuolation (also in females given 2.3 mg/kg/day), which was not accompanied by adverse changes in laboratory tests measuring liver function. Therefore, the no-observed-effect-level (NOEL) was 2.3 mg/kg/day for males and 0.7 mg/kg/day for females, with a NOAEL of 7 mg/kg/day.

Example 21

Retinal Toxicity of CPP-115 in Rats

A retinotoxicity study was performed in Wistar Albino rats treated with CPP-115 (20 mg/kg/day i.p.), vigabatrin (200 mg/kg/day i.p.), or vehicle (0 mg/kg/day i.p.) once daily for either 45 consecutive days (5/sex/group) or 90 consecutive days (10/sex/group). At the conclusion of dosing, rats entered a wash-out period (5-7 days) after which electroretinograms (ERGs) for scotopic (rod), mesopic (standard combined), photopic (cone), and 10 Hz and 15 Hz3 flicker ERG responses were collected for both eyes from each rat. ERG responses in rats treated with CPP-115, at doses 20 to 40 times higher than needed to treat addiction in rats, exhibited reductions in ERG responses, compared to control rats, but less than the reductions observed in rats treated with vigabatrin at the same dose needed to treat addiction in rats.

A greater reduction in all ERG measurements was observed in females compared to males. Only the 15 Hz flicker responses are reported because the 15 Hz ERG responses exhibit smaller rod contributions due to the higher stimulus frequency and would, therefore, be more indicative of cone photoreceptor recovery time.

The ERG results for vigabatrin treatment in this study are similar to past reports of ERG deficits in animal models and individuals. The cumulative data from this study support the potential for CPP-115 to have an improved retinal safety profile compared to vigabatrin. As statistically analyzed by Sinclair Laboratories, CPP-115 showed sporadic observations of statistically significant differences in isolated mean ERG parameter values in 7 of 52 statistical comparisons. These findings are considered to be incidental because there was no observed pattern in findings of amplitude or implicit timing effect differences between CPP-115 and placebo. In contrast, the vigabatrin-treated group showed statistically significant differences between vigabatrin and placebo in 29 of 52 statistical comparisons. In addition, there appeared to be a gender difference in amplitude reduction and implicit time delay with females being more greatly affected than males. Therefore, vigabatrin at a dosage of 200 mg/kg produced significant changes in electroretinal function evident at 45 days maintained out to 90 days. On the other hand, it would appear that the dose level of CPP-115 (20 mg/kg) does not produce consistent significant changes in electroretinal function in rod or cone activity at 45 or 90 days.

Quantitative histological examinations of retinas of the rats from this study were also carried out. Cone receptors were stained with a cone arrestin antibody and counterstained with a red stain for visualization and counting. Retinal sections were also stained with H&E and the ONL nuclei counts and ONL thicknesses were determined. In all cases, the measurements were conducted at three inferior and three superior locations on the retina approximately evenly spaced from the far peripheral inferior location to the far peripheral superior location on the retina.

There was no statistically significant change to the cone receptor counts among the three groups. However, there was a statistically significant change to the ONL nuclei counts and ONL thickness between vigabatrin and the control group. There was no significant change between CPP-115 and the control group. Overall, the data corroborates the ERG observations that females were more affected than males and vigabatrin exposure results in more retinal histological complications than CPP-115.

Example 22

Genotoxicity

CPP-115 was tested in the in vitro mammalian chromosome aberration test using human peripheral blood lymphocytes (HPBL) in both the absence and presence of an Aroclor-induced rat liver S9 metabolic activation system. The percentage of cells with structural or numerical aberrations in the test article-treated groups was not significantly increased compared to the solvent control group at any dose levels tested (535, 1070, and 2140 µg/mL). Thus, it was concluded that CPP-115 was not elastogenic in the in vitro chromosome aberration test in human lymphocytes.

The potential for CPP-115 to induce reverse mutations was evaluated using 4 tester strains of *Salmonella typhimurium* (TA98, TA100, TA1535, and TA1537) and 1 *Escherichia coli* tester strain (WP2uvrA) in the presence or absence of Aroclor-induced rat liver S9. No positive mutagenic response was observed across the range of CPP-115 concentrations tested in an initial toxicity-mutation assay (1.5, 5.0, 15, 50, 150, 500, 1500, and 5000 µg per plate) or in the confirmatory mutagenicity assay (50, 150, 500, 1500, and 5000 µg per plate). Neither precipitate nor appreciable toxicity was observed in the initial and confirmatory assays. Thus, it was concluded that CPP-115 was not mutagenic in the in vitro bacterial reverse mutation assay.

Example 23

Interaction of CPP-115 with GABA Transporters

Plasmids encoding hGAT-1, hBGT-1, hGAT-2, and hGAT-3 were transfected into tsA201 cells. The next day tsA201 cells transiently expressing each of the 4 GABA transporter subtypes were plated followed by (36 to 48 hours later) addition of [3H]GABA (30 nM) and CPP-115 (1 mM). Uptake of [3H]GABA was determined after incubation at 37° C. for 3 minutes. The $IC_{50}$ was >1000 µM for each GABA transporter subtype, thus CPP-115 did not affect GABA uptake in recombinantly-expressed human GABA transporters.

In vitro expression of cytochrome P450 enzymes preparations of cultured human hepatocytes were treated once daily for 3 consecutive days with dimethyl sulfoxide (DMSO, 0.1% v/v, vehicle control), 1 of 3 concentrations of CPP-115 (1, 10, or 100 µM) or 1 of 3 known human cytochrome P450 (CYP) inducers, i.e., omeprazole (100 µM), phenobarbital (750 µM), and rifampin (10 µM). Cells were then incubated with appropriate marker substrates and analyzed for CYP activity. Treatment of the hepatocyte cultures with CPP-115 neither increased nor decreased the activities of CYP1A2, CYP2B6, and CYP3A4/5 at any of the concentrations tested as compared to vehicle control cultures, whereas the positive controls caused anticipated increases in CYP activities. Thus, under the conditions of this study, CPP-115, at concentrations up to 100 µM, was not an inducer of CYP1A2, CYP2B6, and CYP3A4/5 activity in primary human hepatocytes.

Human liver microsomes from a pool of 16 individuals were incubated with 2 different marker substrates in the presence and absence of CPP-115 at concentrations ranging from 0.1 to 100 µM. To evaluate time- and metabolism-dependent inhibition, CPP-115 was preincubated with human liver microsomes in the presence and absence of a b-nicotinamide adenine dinucleotide phosphate (NADPH)-generating system for 30 minutes before incubation with the marker substrate. Known direct-acting and metabolism-dependent inhibitors of CYP enzymes were included as positive controls. Under the experimental conditions examined, there was little or no evidence of direct inhibition of CYP1A2, CYP2B6, CYP2C8, CYP2C9, CYP2C19, CYP2D6, or CYP3A4/5 (as measured by testosterone 6β-hydroxylation and midazolam 1'-hydroxylation) by CPP-115. Additionally, there was little or no evidence of either time- or metabolism-dependent inhibition of any of the CYP enzymes evaluated by CPP-115.

Example 24

Metabolic Stability in Cryopreserved Human Hepatocytes

The metabolic stability of CPP-115 was evaluated in cryopreserved human hepatocytes using a LC/MS/MS method. Cryopreserved human hepatocytes were prepared from a pool of 3 individuals (1,000,000 cells/mL) and incubated in triplicate with CPP-115 (5 µM) for 0, 10, 60, 120, and 240 minutes. Little loss of CPP-115 occurred during the course of incubation (ranging from 6% at 10 minutes to 16% at 240 minutes), consistent with a drug that survives first-pass metabolism and through several half lives in the blood stream.

Example 25

Effect of CPP-115 on Cloned hERG Potassium Channels

The in vitro effects of CPP-115 were evaluated on the hERG (human ether-à-go-go-related gene) channel current (a surrogate for IKr, the rapidly activating, delayed rectifier cardiac potassium current). Two concentrations of CPP-115 (10 and 300 µM) were tested at near-physiological temperature. CPP-115 inhibited hERG potassium current by a mean of 1.1% at 10 µM (n=3) and 1.5% at 300 µM (n=3) versus 0.8% for vehicle controls (n=3). hERG inhibition at both test concentrations was not statistically significant (p<0.05) when compared to vehicle control values, indicating a minimal risk for CPP-115 induced cardiac arrhythmias. The $IC_{50}$ for the inhibitory effect of CPP-115 on hERG potassium current was not calculated due to the lack of significant inhibition. Under identical conditions, the positive control (60 nM terfenadine) inhibited hERG potassium current by a mean of 85.3% (n=2). The effect of terfenadine confirms the sensitivity of the test system to hERG inhibition.

Example 26

Results of Clinical Trials Using CPP 115

In a Phase I randomized, double-blind, placebo-controlled, parallel-group, safety, tolerability and pharmacokinetic study of single ascending oral doses of CPP-115 were determined. Each subject received a single dose of either CPP-115 or matching placebo, in a composition with fruit juice (e.g., Ocean Spray™ Blueberry Pomegranate Juice), followed by repeated observations for each of the study objectives.

The starting dose for this first-in-man study of CPP-115 was determined to be 5 mg/day for a 60 kg person based on preclinical toxicity studies in dogs and rats that identified a "No Observed Adverse Effect Level" (NOAEL) of 6 and 2.3 mg/kg/day in rats and dogs, respectively (Human Equivalent Dose [HED]=0.96 and 1.24 mg/kg/day, in rats and dogs, respectively). Using the most sensitive species (rat), and assuming a 60 kg weight, a maximum recommended starting dose was calculated to be 5 mg. This calculation assumes application of a safety factor of 10.

As a matter of protocol, six sequentially increasing dose levels of CPP-115 can be studied, starting at 5 mg and proceeding stepwise through 13, 32, 80, 200 and 500 mg, and matching placebo. Alternatively, a dose response relationship can be developed beginning at the highest dose permitted by government regulation and adjusting dosage downward until no effect is observed. Each dose cohort consisted of 8 subjects. A second 13 mg dose group was recruited when the initial 13 mg treatment group (Cohort 2) was found to have unusually high levels of potassium at Day 3. Within each dose cohort, subjects were randomized to receive CPP-115 or matching placebo in a 3:1 ratio. Subjects were followed for safety for a 30-day period after receiving their single dose of study treatment.

This study investigated the pharmacokinetics (PK) of CPP-115. Blood and urine samples for PK analysis were collected at multiple, scheduled times during the study beginning at pre-dose on Day 1 and up to 48 hours post-dose. Concentrations of CPP-115 were measured in plasma and urine.

Dose escalation can continue until completion of the 500 mg dose cohort. The MTD was defined as the highest dose evaluated that did not cause any unacceptable study drug related toxicities. (Top dose studied of 500 mg is more than 10 times greater than the predicted effective doses from animal models of 15-30 mg/day.) Using the aforementioned alternative dosage protocol, up to about 80 mg/day of compound CPP-115 can be used effectively.

Summary of results: no serious or severe adverse events; no cardiovascular or respiratory events; rapidly absorbed (time to peak blood concentration approximately 30 minutes); elimination half-life of 4-6 hours; cmax increased in a dose proportional manner over the range of doses studied; there was a greater than proportional increase in AUCs In accordance with this invention, various other compounds, varied structurally, stereochemically and/or configurationally, are available through such incorporated synthetic procedures and techniques or straight-forward modifications thereof, such modifications as would also be known and understood by those skilled in the art and made aware of this invention, such procedures, techniques and modifications limited only by the commercial or synthetic availability of any corresponding reagent or starting material.

We claim:
1. A method for the treatment of hepatocellular carcinoma in a human subject in need thereof, said method comprising administering to said subject a therapeutically effective amount of a compound of a formula

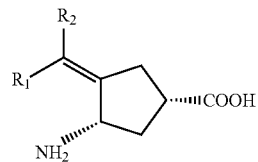

wherein $R_1$ and $R_2$ are selected from H and F, and at least one of $R_1$ and $R_2$ is F; or a salt thereof.

2. The method of claim 1 wherein $R_1$ and $R_2$ are F.
3. The method of claim 2 wherein said administration is oral.
4. The method of claim 3 wherein said amount of said compound is about 0.001 mg/60 subject kg/day-about 10,000 mg/60 subject kg/day.
5. The method of claim 4 wherein said amount of said compound is about 32 mg/60 subject kg/day-about 200 mg/60 subject kg/day.
6. The method of claim 5 wherein said amount is about 80 mg/60 subject kg/day.
7. The method of claim 2 wherein said compound is provided in a pharmaceutical composition.
8. A method of reducing activity of an ornithine aminotransferase expressed by a human hepatocellular carcinoma, said method comprising:
providing a compound of a formula

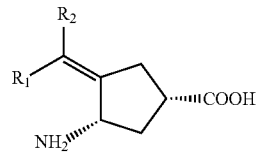

wherein $R_1$ and $R_2$ are selected from H and F, and at least one of $R_1$ and $R_2$ is F; or a salt thereof; and
contacting a cellular medium comprising a hepatocellular carcinoma expressing an ornithine aminotransferase with an amount of said compound effective to reduce ornithine aminotransferase activity, thereby reducing glutamate production in said cellular medium.
9. The method of claim 8 wherein $R_1$ and $R_2$ are F.
10. The method of claim 9 wherein said compound is provided in a pharmaceutical composition.
11. The method of claim 9 wherein such contact is in vivo.
12. The method of claim 11 wherein said contact is with a human subject in need thereof.

13. The method of claim 12 wherein said contact comprises oral administration.

14. The method of claim 13 wherein said amount of said compound is about 0.001 mg/60 subject kg/day-about 10,000 mg/60 subject kg/day.

15. The method of claim 14 wherein said amount of said compound is about 32 mg/60 subject kg/day-about 200 mg/60 subject kg/day.

16. The method of claim 15 wherein said amount is about 80 mg/60 subject kg/day.

17. The method of claim 12 wherein said compound is provided in a pharmaceutical composition.

* * * * *